(12) United States Patent
Santi et al.

(10) Patent No.: US 6,946,482 B2
(45) Date of Patent: Sep. 20, 2005

(54) MOTILIDE COMPOUNDS

(75) Inventors: Daniel V. Santi, San Francisco, CA (US); Brian Metcalf, Moraga, CA (US); Christopher Carreras, San Carlos, CA (US); Yaoquan Liu, Castro Valley, CA (US); Robert McDaniel, Palo Alto, CA (US); Eduardo J. Rodriguez, Mountain View, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 140 days.

(21) Appl. No.: 10/648,946

(22) Filed: Aug. 26, 2003

(65) Prior Publication Data

US 2004/0138150 A1 Jul. 15, 2004

Related U.S. Application Data

(60) Provisional application No. 60/407,345, filed on Aug. 29, 2002.

(51) Int. Cl.$^7$ ............................................. A61K 31/35
(52) U.S. Cl. ...................................... 514/450; 549/271
(58) Field of Search ........................... 514/450; 549/271

(56) References Cited

U.S. PATENT DOCUMENTS

| | | | |
|---|---|---|---|
| 4,382,085 A | 5/1983 | Sciavolino et al. | 424/180 |
| 4,382,086 A | 5/1983 | Sciavolino et al. | 424/180 |
| 4,857,641 A | 8/1989 | Hauske et al. | 536/73 |
| 4,916,134 A | 4/1990 | Ueda et al. | 514/294 |
| 5,190,871 A | 3/1993 | Cox et al. | 435/172.3 |
| 5,288,709 A | 2/1994 | Freiberg et al. | 514/29 |
| 5,523,401 A | 6/1996 | Freiberg et al. | 540/457 |
| 5,523,418 A | 6/1996 | Freiberg et al. | 549/270 |
| 5,538,961 A | 7/1996 | Freiberg et al. | 514/183 |
| 5,554,605 A | 9/1996 | Freiberg et al. | 514/183 |
| 5,578,579 A | 11/1996 | Lartey et al. | 514/29 |
| 5,658,888 A | 8/1997 | Koga et al. | 514/29 |
| 5,712,253 A | 1/1998 | Lartey et al. | 514/28 |
| 5,824,513 A | 10/1998 | Katz et al. | 435/76 |
| 5,922,849 A | 7/1999 | Premchandran et al. | 536/7.2 |
| 6,066,721 A | 5/2000 | Khosla et al. | 536/23.1 |
| 6,077,943 A | 6/2000 | Omura et al. | 536/7.2 |
| 6,080,555 A | 6/2000 | Khosla et al. | 435/41 |
| 6,084,079 A | 7/2000 | Keyes et al. | 536/7.2 |
| 6,169,168 B1 | 1/2001 | Asaka et al. | 536/7.4 |
| 6,251,636 B1 | 6/2001 | Betlach et al. | 435/76 |
| 6,261,816 B1 | 7/2001 | Khosla et al. | 435/183 |
| 6,391,594 B1 | 5/2002 | Khosla et al. | 435/91.4 |
| 6,395,710 B1 | 5/2002 | Chu et al. | 514/29 |
| 6,403,775 B1 | 6/2002 | McDaniel | 536/7.2 |
| 6,437,151 B2 | 8/2002 | Leadlay et al. | 549/271 |
| 6,562,795 B2 | 5/2003 | Ashley et al. | 514/29 |
| 2002/0004229 A1 | 1/2002 | Santi et al. | 435/76 |
| 2002/0094962 A1 | 7/2002 | Ashley et al. | 514/28 |
| 2002/0192709 A1 | 12/2002 | Carreras et al. | 435/7.1 |
| 2003/0220271 A1 | 11/2003 | Ashley et al. | 514/28 |

FOREIGN PATENT DOCUMENTS

| | | |
|---|---|---|
| EP | 0119431 B1 | 9/1987 |
| JP | 60-218321 | 11/1985 |
| WO | WO 99/21867 A1 | 5/1999 |
| WO | WO 00/44717 A2 | 8/2000 |
| WO | WO 01/27284 A2 | 4/2001 |
| WO | WO 01/31035 A2 | 5/2001 |
| WO | WO 01/83803 A1 | 11/2001 |
| WO | WO 2004/013153 A2 | 2/2004 |

OTHER PUBLICATIONS

Pariza, RJ et al 'Erythromycin: new chemistry on an old compound' Pure & Appl. Chem., vol. 66 (10/11) 2365–2368 (1994).*

Gordin, A et al 'Concentrations of erythromycin, 2-acetyl erythromycin, and their anhydro forms in plasma and tonsillar tissue after repeated dosage of erythromycin stearate and erythromycin acistrate' Antimicrobial Agents&Chemotherapy, 1988, 1019–1024.*

Carreras et al., "*Saccharopolyspora erythraea*–catalyzed bioconversion of 6–deoxyerythronolide B analogs for production of novel erythromycins," *J. Biotechnology*, 92, 217–228 (2002).

Carreras et al., "Stable Expression of a Synthetic Gene for the Human Motilin Receptor: Use in an Aequorin–Based Receptor Activation Assay," *Anal. Biochem.* 300, 146–15.

(Continued)

Primary Examiner—Amelia A. Owens
(74) Attorney, Agent, or Firm—Yuan Chao

(57) ABSTRACT

Motilide compounds having the formula (I),

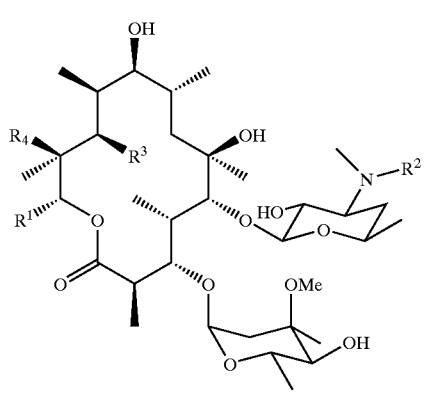

wherein $R^1$, $R^2$, $R^3$, and $R^4$ are as defined herein, and methods for their preparation and use in the treatment of diseases or conditions characterized by impaired gastric motility.

14 Claims, No Drawings

OTHER PUBLICATIONS

Frykman et al., "Precursor–Directed Production of Erythromycin Analogs by *Saccharopolyspora erythraea*," *Biotechnol. Bioeng.*, 76, 303–310 (2001).

Ku et al., "Synthesis and Antibacterial Activities of Novel 12–O–Methylerythromycin A Derivatives," *J. Antibiotics* 52(10), 908–912 (Oct. 1999).

Ku et al., "Synthesis of a Novel Macrolide: 9(S)–9–Dihydro–12–O–Methylerythromycin A via Regioselective Methylation," *J. Org. Chem.*, 64, 2107 (1999).

Omura et al., "Gastrointestinal motor–stimulating activity of macrolide antibiotics and the structure–activity relationship," *J. Antibiotics* (1985) 38: 1631–2.

Rodriguez et al., *J. Ind. Microbio. Biotechnol.*, "Rapid Engineering of Polyketide Overproduction by Gene Transfer to Industrially Optimized Strains," web–published as document No. 10.1007/s10295–003–0045–1 (http://link.springer–ny.com) (Apr. 16, 2003).

Xue et al., "A Multiplasmid approach to preparing large libraries of polyketides," *Proc. Natl. Acad. Sci. U.S.A.*, 96, 11740–11745 (1999).

Chemical Abstracts No. 104:82047 (abstract of JP 60–218321).

Chemical Abstracts No. 130:325342 (abstract of WO 99/21867).

Chem. Abs. 90:152561 (abstract of PL 97877).

Hauske et al., "Regiospecific Synthesis of 9–Desoxoerythromycin A," *J. Org. Chem.*, 49, 712–714 (1984).

Hauske et al., "Aglycon Modifications of Erythromycin A: Regiospecific and Stereo–selective Elaboration of the C–12 Position," *J. Org. Chem.*, 52, 4622–4625 (1987).

Faghih et al., "Synthesis and Antibacterial Activity of (9S)–9–Dihydroclarithromycin," *J. Antibiotics*, 43, 1334–1336 (1990).

Hauske et al., "Synthesis of 10,11–Anhydroerythromycin," *J. Org. Chem.*, 47, 1595–1596 (1982).

Hauske et al., "Aglycon Modifications of Erythromycin A and Erythromycin B: Regio–specific Nucleophilic Ring Opening of Cyclic Thionocarbonates," *J. Org. Chem.*, 48, 5138–5140 (1938).

Faghih et al., "Motilides and motilactides: design and development of motilin receptor agonists as a new class of gastrointestinal prokinetic drugs," *Drugs Fut.*, 23 (8), 861–872 (1998).

Depoortere et al., "Structure–Activity Relation of Erythromycin–Related Macrolides in Inducing Contractions and in Displacing Bound Motilin in Rabbit Duodenum," *J. Gastrointestinal Motility*, 1, 150–159 (1989).

Faghih et al., "Preparation of 9–deoxo–4"–deoxy–6,9–epoxyerythromycin lactams "motilactides": potent and orally active prokinetic agents, *Bioorg. Med. Chem. Lett.*, 8, 805–810 (1998).

* cited by examiner

MOTILIDE COMPOUNDS

CROSS-REFERENCE TO RELATED APPLICATIONS

This application claims the benefit of U.S. Provisional Application No. 60/407,345, filed Aug. 29, 2002; the disclosure of which is incorporated herein by reference.

BACKGROUND OF THE INVENTION

1. Field of the Invention

The present invention provides prokinetic agents with superior pharmacological and pharmacokinetic properties for the treatment of gastrointestinal motility disorders. The invention relates to the fields of chemistry, medicinal chemistry, medicine, molecular biology, and pharmacology.

2. Description of Related Art

Gastrointestinal ("GI") motility regulates the orderly movement of ingested material through the gut to insure adequate absorption of nutrients, electrolytes and fluids. Appropriate transit through the esophagus, stomach, small intestine and colon depends on regional control of intraluminal pressure and several sphincters that regulate forward movement and prevent back-flow of GI contents. The normal GI motility pattern may be impaired by a variety of circumstances including disease and surgery.

Disorders of gastrointestinal motility include, for example, gastroparesis and gastroesophageal reflux disease ("GERD"). Gastroparesis is the delayed emptying of stomach contents. Symptoms of gastroparesis include stomach upset, heartburn, nausea, and vomiting. Acute gastroparesis may be caused by, for example, drugs (e.g., opiates), viral enteritis, and hyperglycemia, and is usually managed by treating the underlying disease rather than the motility disorder. The most common causes of chronic gastroparesis are associated with long standing diabetes or idiopathic pseudo-obstruction, often with so-called "non-ulcer" or "functional" dyspepsia.

GERD refers to the varied clinical manifestations of reflux of stomach and duodenal contents into the esophagus. The most common symptoms are heartburn and dysphasia; blood loss may also occur from esophageal erosion. GERD may be associated with low tone and inappropriate relaxation of the lower esophageal sphincter and occurs with gastroparesis in about 40% of cases. In most cases, GERD appears to be treatable with agents that reduce the release of acidic irritant by the stomach (e.g., Prilosec) or agents that increase the tone of the lower esophageal sphincter (e.g., cisapride). Other examples of disorders whose symptoms include impaired gastrointestinal motility are anorexia, gall bladder stasis, postoperative paralytic ileus, scleroderma, intestinal pseudoobstruction, gastritis, emesis, and chronic constipation (colonic inertia).

These GI disorders are generally treated with prokinetic agents that enhance propulsive motility. Motilides are macrolide compounds such as erythromycin and its derivatives that are agonists of the motilin receptor. Evidence of the potential clinical utility of motilides includes their ability to induce phase III of Migrating Motor Complexes ("MMC"). MMC refers to the four phases (I–IV) of electrical activity displayed by the stomach and small intestine in the fasting state. Muscular contraction occurs in phases III and IV, coincident with a peristaltic wave that propels enteric contents distally during fasting. Other clinically relevant effects include: increase in esophageal peristalsis and LES pressure in normal volunteers and patients with GERD; acceleration of gastric emptying in patients with gastric paresis; and stimulation of gallbladder contractions in normal volunteers, patients after gallstone removal, and diabetics with autonomic neuropathy.

The erythromycins are a family of macrolide antibiotics made by the fermentation of the Actinomycetes *Saccharopolyspora erythraea* (formerly *Streptomyces erythreus*). Erythromycin A, a commonly used antibiotic, is the most abundant and important member of the family.

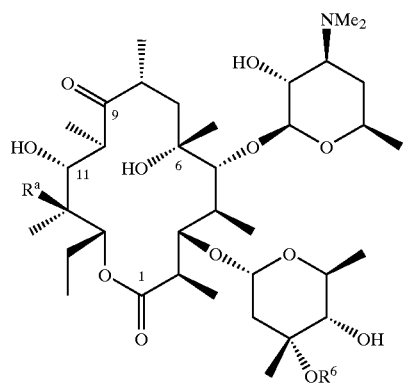

| | | |
|---|---|---|
| Erythromycin A | $R^a$ = OH | $R^b$ = Me |
| Erythromycin B | $R^a$ = H | $R^b$ = Me |
| Erythromycin C | $R^a$ = OH | $R^b$ = H |
| Erythromycin D | $R^a$ = H | $R^b$ = H |

Since the 1950's, erythromycin A (1) has been known to cause GI side effects such as nausea, vomiting, and abdominal discomfort. Erythromycin A undergoes acid catalyzed degradation in the stomach, forming initially 8,9-anhydro-6,9-hemiacetal 2 (also known as erythromycin A enol ether) and then spiroketal 3, as shown in Scheme A. The GI side effects are largely explained by motilin agonist activity in erythromycin A itself and hemiacetal 2. (Spiroketal 3 is inactive.)

SCHEME A

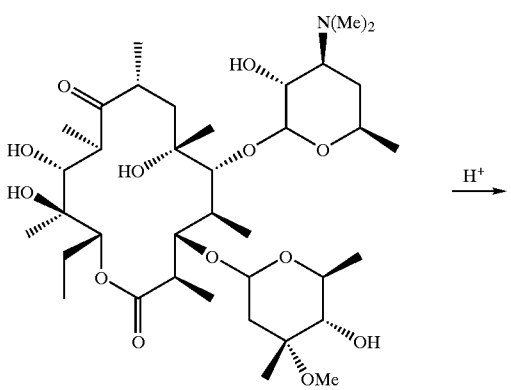

(1) (Erythromycin A)

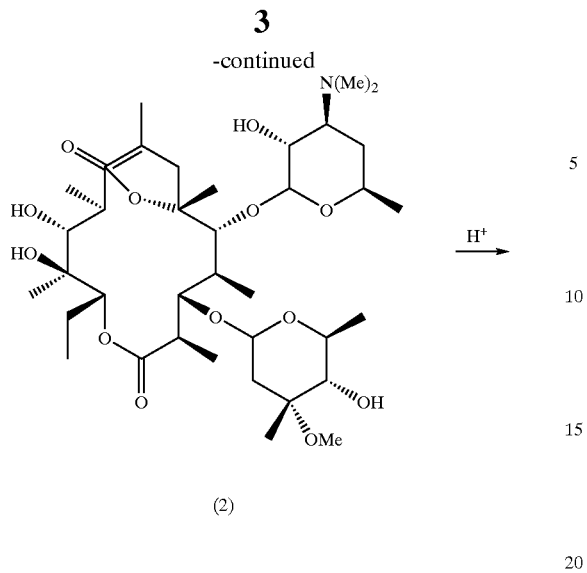

(2)

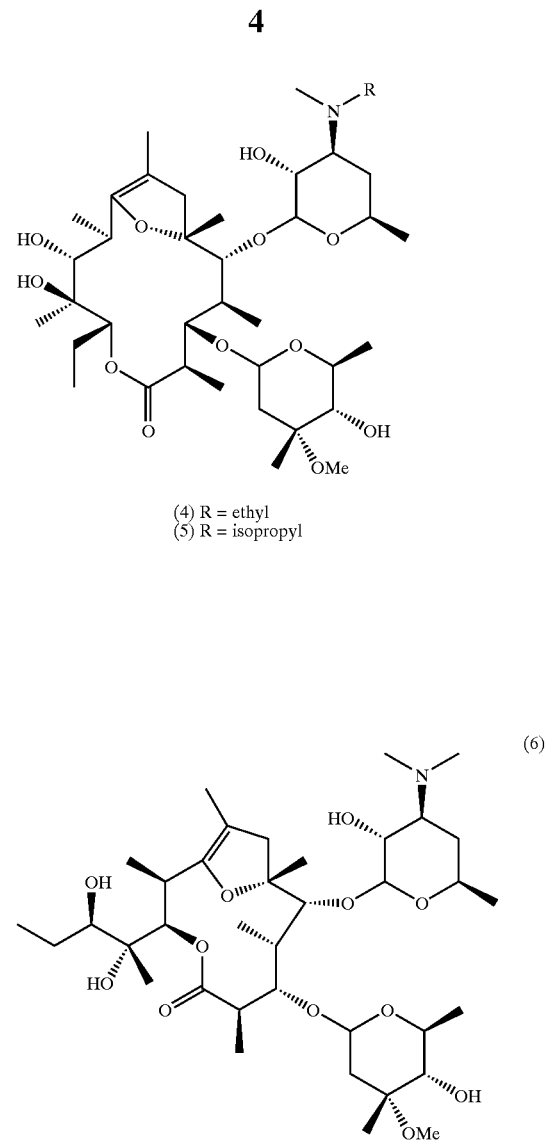

(4) R = ethyl
(5) R = isopropyl (6)

(7)

and

Omura et al., "Gastrointestinal motor-stimulating activity of macrolide antibiotics and the structure-activity relationship," *J. Antibiotics* (1985) 38: 1631–2, discloses the relative ability of erythromycin A, 9-dihydroerythromycin A, and other macrolides to stimulate gut contraction in conscious dogs. In this assay, 9-dihydroerythromycin A was reported to be 65% as active as erythromycin at a dose of 1 mg/kg. As 9-dihydroerythromycin cannot form an enol ether, it is clear that enol ether formation is not essential for motilide activity. Erythromycin A is currently used to treat motility disorders, even though its antibacterial activity raises concerns over generation of resistant microorganisms. As 9-dihydroerythromycin also shows antibacterial activity, there are similar concerns with its use as a motilide.

A number of erythromycin enol ether analogs have been prepared as motilides, including EM-523 (4); EM-574 (5); LY267,108 (6); GM-611 (7); and ABT-229 (8) whose structures are shown below. See U.S. Pat. Nos. 5,578,579; 5,658,888; 5,922,849; 6,077,943; and 6,084,079; each of which is incorporated herein by reference.

-continued

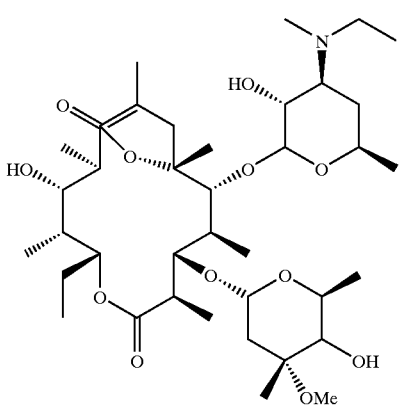

(8)

Other motilides of interest include lactam enol ethers and lactam epoxide derivatives. See U.S. Pat. Nos. 5,712,253; 5,523,401; 5,523,418; 5,538,961; and 5,554,605; each of which is incorporated herein by reference.

Despite the high potency of the erythromycin enol ethers as motilides, their metabolic instability has hindered their development in the clinic. Further, compounds such as 7 and 8 show motilin receptor desensitization in both cell-based and muscle strip contractility assays. This desensitization may portend a decrease in efficacy upon multiple dosing of the motilide.

There thus exists a need for new motilide compounds having decreased antibacterial activity, increased metabolic stability, and decreased receptor desensitization. The present invention provides analogs of 9-dihydroerythromycin that meet this need.

BRIEF SUMMARY OF THE INVENTION

One aspect of the present invention provides compounds having the formula (I):

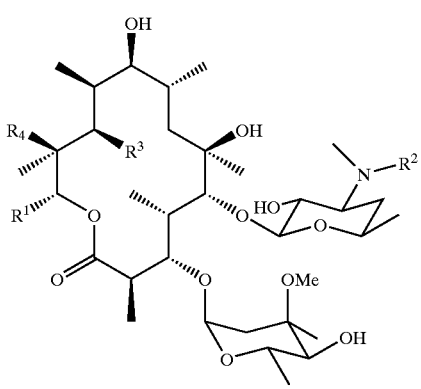

(I)

and the pharmaceutically acceptable salts, esters, and prodrug forms thereof, wherein $R^1$ is substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, or substituted or unsubstituted heterocyclo; $R^2$ is H, substituted or unsubstituted $C_1$–$C_5$ alkyl, substituted or unsubstituted $C_2$–$C_5$ alkenyl, substituted or unsubstituted $C_2$–$C_5$ alkynyl, substituted or unsubstituted aryl, or substituted or unsubstituted heterocyclo; $R^3$ is H or OH; and $R^4$ is H or OH, or $R^3$ and $R^4$ taken together form O—C(=O)—O, with the proviso that when (a) $R^1$ is ethyl and (b) $R^3$ is OH or $R^3$ and $R^4$ taken together form O—C(=O)—O, then $R^2$ is not H or methyl.

In a second aspect, there is provided a method for treating a disorder of gastric motility in a patient suffering therefrom, comprising administering to the patient a therapeutically effective dose of a composition of this invention.

In a third aspect, there is provided a pharmaceutical composition comprising a compound of this invention and a pharmaceutically acceptable carrier.

In a fourth aspect, compounds (I) of this invention are used for the preparation of a medicament for treating a gastric motility disorder in a subject.

In a fifth aspect, this invention provides a recombinant host cell that produces 11-deoxyerythromycins (particularly 11-deoxyerythromycin B), along with the modified polyketide synthase genes they express and the vectors that are used to engineer them. The 11-deoxyerythromycins are useful as intermediates for the synthesis of compounds of this invention. The recombinant host cell has an eryAI gene engineered by replacement of the ketoreductase domain in module 2 thereof with a cassette containing a dehydratase domain, an enoylreductase domain, and a ketoreductase domain. In a sixth aspect, this invention provides a method of making 11-deoxyerythromycins, comprising culturing such a recombinant host cell.

DETAILED DESCRIPTION OF THE INVENTION

Definitions

The definitions of the terms given below apply to the terms as they are used throughout this specification and the appended claims, unless the context clearly indicates otherwise.

"Alkyl" means a straight or branched chain hydrocarbon moiety having the specified number of carbon atoms in the chain or, where the number of carbon atoms is not specified, up to 5 carbon atoms in the chain.

"Alkenyl" means a straight or branched chain hydrocarbon moiety having at least one carbon-carbon double bond and the specified number of carbon atoms in the chain or, where the number of carbon atoms is not specified, up to 5 carbon atoms in the chain.

"Alkynyl" means a straight or branched chain hydrocarbon moiety having at least one carbon-carbon triple bond and the specified number of carbon atoms in the chain or, where the number of carbon atoms is not specified, up to 5 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring which may be further fused with an unsaturated $C_3$–$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine and iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

"Pharmaceutically acceptable ester" means an ester that hydrolyzes in vivo (for instance in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Where a group is characterized as being substituted (as in "substituted alkyl," substituted alkenyl," etc.), such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. The substituent may be further substituted, for example, by halo, hydroxy, alkyl, alkoxy; aryl, substituted aryl, substituted alkyl, substituted aralkyl, and the like.

Unless particular stereoisomers are specifically indicated (e.g., by a bolded or dashed bond at a relevant stereocenter in a structural formula), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in *Design of Prodrugs*, Bundgaard, ed., Elsevier, 1985.

Compounds and Methods

In one embodiment, compounds having the formula (I) are provided wherein $R^1$ is substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, or substituted or unsubstituted heterocyclo; $R^2$ is H, ethyl, propyl, isopropyl, or 2-butyl; $R^3$ is H or OH; and $R^4$ is H or OH, or $R^3$ and $R^4$ taken together form O—C(=O)—O, with the proviso that when $R^1$ is ethyl and $R^3$ is OH or $R^3$ and $R^4$ taken together form O—C(=O)—O then $R^2$ is not H or methyl.

In another embodiment of the invention, compounds having formula (I) are provided wherein $R^1$ is substituted or unsubstituted $C_1$–$C_5$ alkyl; $R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O, with the proviso that when (a) $R^1$ is ethyl and (b) $R^3$ is OH or $R^3$ and $R^4$ taken together form O—C(=O)—O, then $R^2$ is not H or methyl.

In another embodiment of the invention, compounds having formula (I) are provided wherein $R^1$ is ethyl; $R^2$ is substituted or unsubstituted $C_2$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is ethyl; $R^2$ is ethyl, propyl, isopropyl, or 2-butyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is substituted ethyl; $R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is fluoroethyl or azidoethyl; $R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is substituted ethyl; $R^2$ is H, ethyl, propyl, isopropyl, or 2-butyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is fluoroethyl or azidoethyl; $R^2$ is H, ethyl, propyl, isopropyl, or 2-butyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is propyl; $R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is propyl; $R^2$ is H, ethyl, propyl, isopropyl, or 2-butyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is vinyl, butyl, benzyl, but-3-en-1-yl, phenyl, or 4-hydroxyphenyl; $R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; $R^3$ is H or OH; and $R^4$ is H or OH, or $R^3$ and $R^4$ taken together form O—C(=O)—O.

In another embodiment of the invention, compounds having formula (I) are provided wherein $R^1$ is vinyl, butyl, benzyl, but-3-en-1-yl, phenyl, or 4-hydroxyphenyl; $R^2$ is H, ethyl, propyl, isopropyl, or 2-butyl; $R^3$ is H or OH; and $R^4$ is H or OH, or $R^3$ and $R^4$ taken together form O—C(=O)—O.

In another embodiment of the invention, having formula (I) are provided, wherein $R^3$ and $R^4$ are independently H or OH; $R^1$ is selected from the group consisting of ethyl, 2-fluoroethyl, and 1-propyl; and $R^2$ is selected from the group consisting of methyl, ethyl, isopropyl, and 2-butyl; with the proviso that when $R^1$ is ethyl and $R^3$ is OH, then $R^2$ is not methyl.

In another embodiment, $R^1$ is substituted or unsubstituted $C_1$–$C_5$ alkyl (preferably ethyl); $R^2$ is H, methyl, ethyl, propyl, isopropyl, or 2-butyl; $R^3$ is H; and $R^4$ is H or OH.

In another embodiment of the invention, there is provided compounds having the structures:

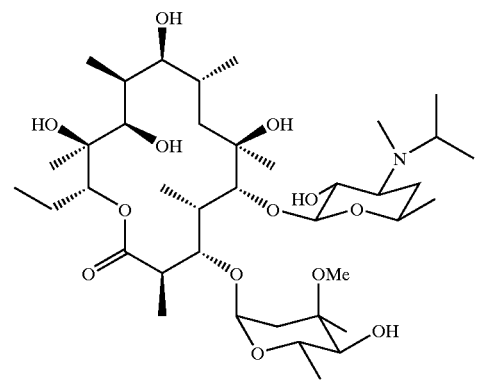

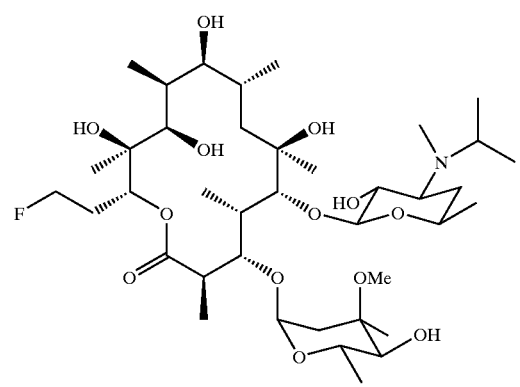

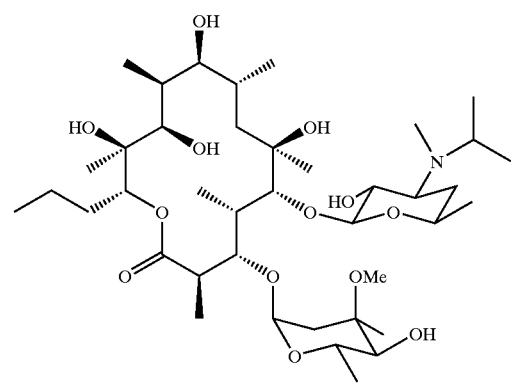

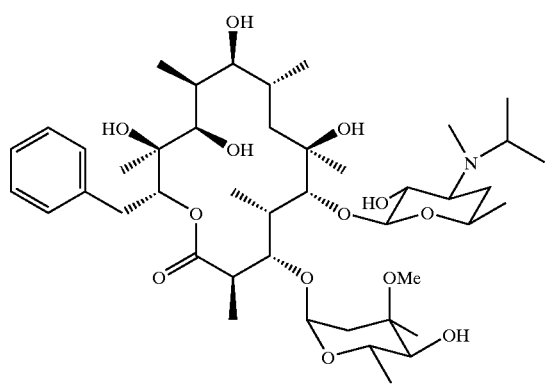

SCHEME 1
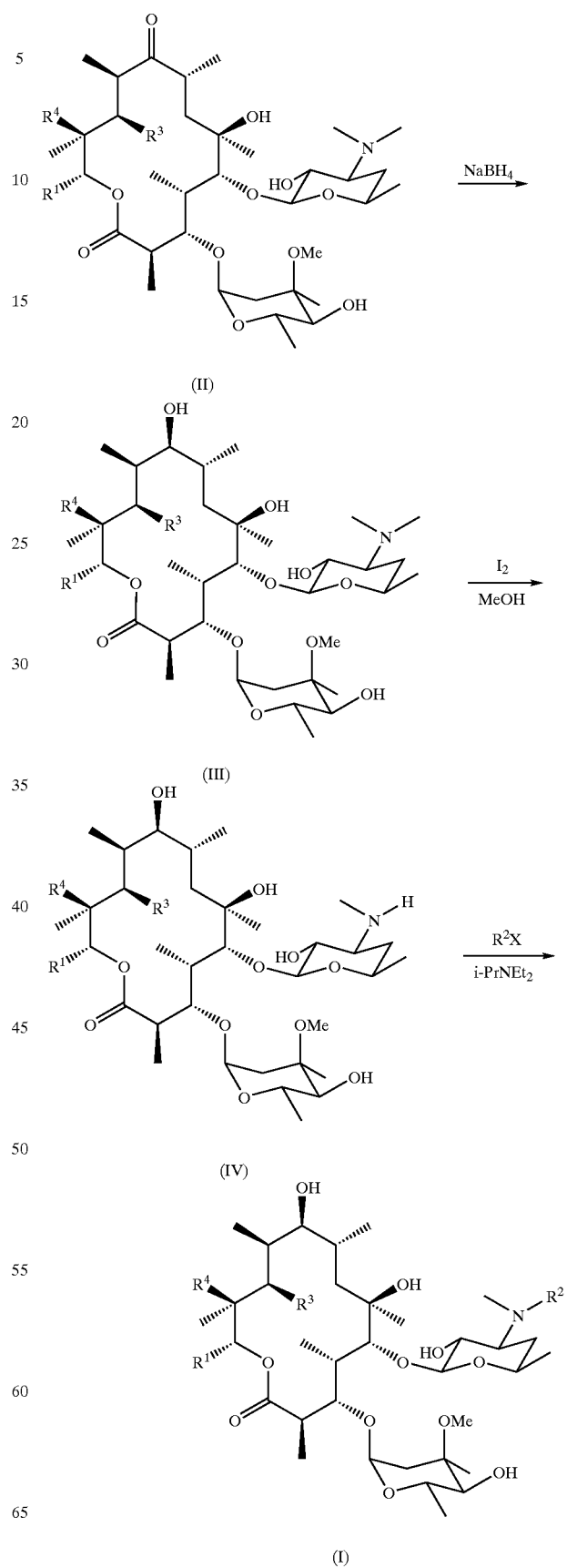
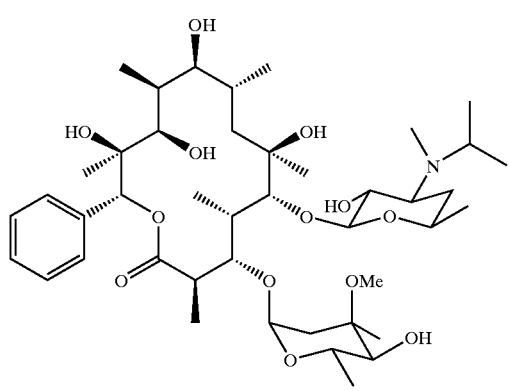
and
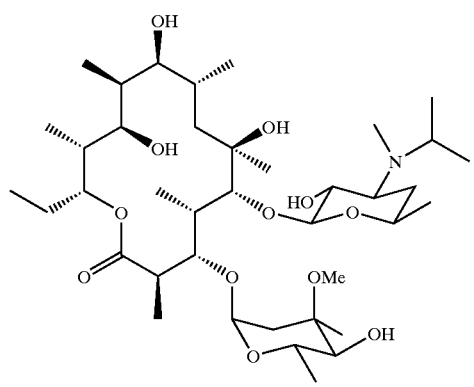
Another aspect of the present invention provides methods for the preparation of the compounds of formula (I). In one embodiment, the compounds of formula (I) are prepared from the corresponding erythromycins (II) as illustrated in Scheme 1.

In this embodiment, the erythromycin (II) is treated with sodium borohydride in methanol at provide the (9S)-9-dihydroerythromycin, (III). Compound (III) is demethylated, for example using iodine and light in buffered methanol or using N-iodosuccinimide in acetonitrile, to provide compound (IV). Alkylation of compound (IV) using R²X, wherein R² is as defined above and X is a halide, preferably bromine or iodine, or sulfonate, preferably triflate or tosylate, in the presence of a base such as N,N-diisopropylethylamine provides the compounds of formula (I).

Alternatively, the sequence of the demethylation/alkylation steps and the borohydride reduction step can be reversed, as shown in Scheme 1A:

SCHEME 1A

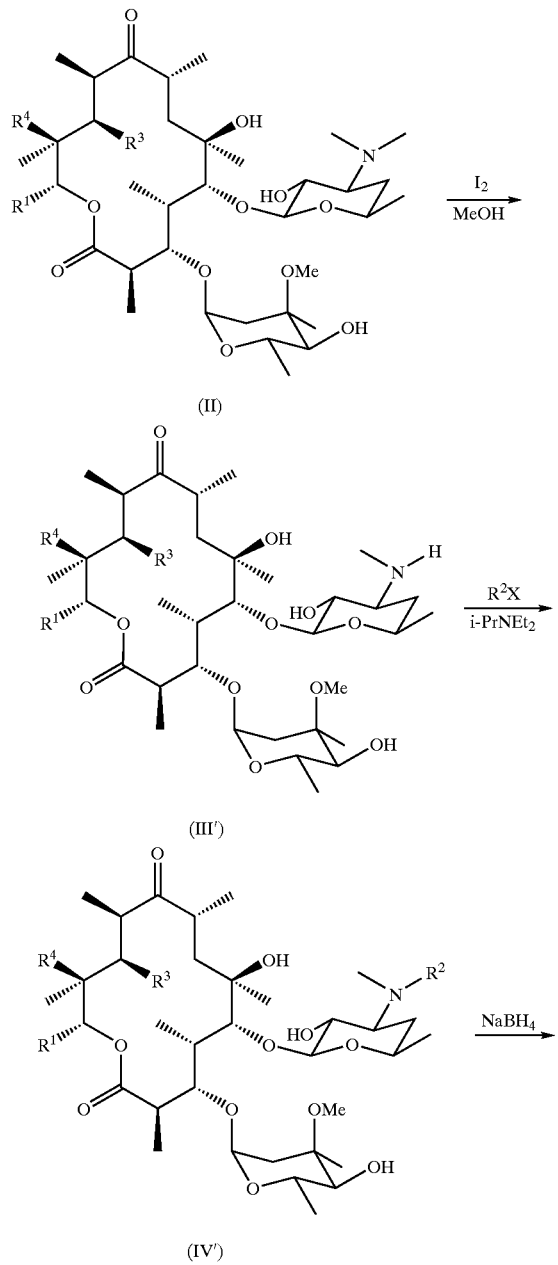

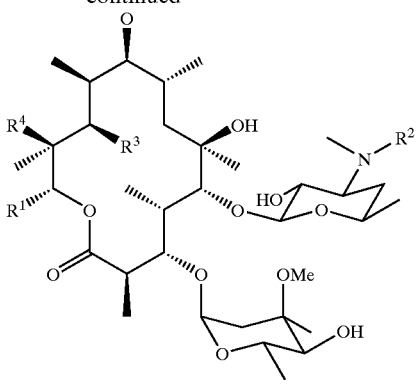

In another embodiment of the invention, the erythromycins (II) wherein $R^3$ and $R^4$ taken together form O—C(=O)—O are prepared as illustrated in Scheme 2.

SCHEME 2

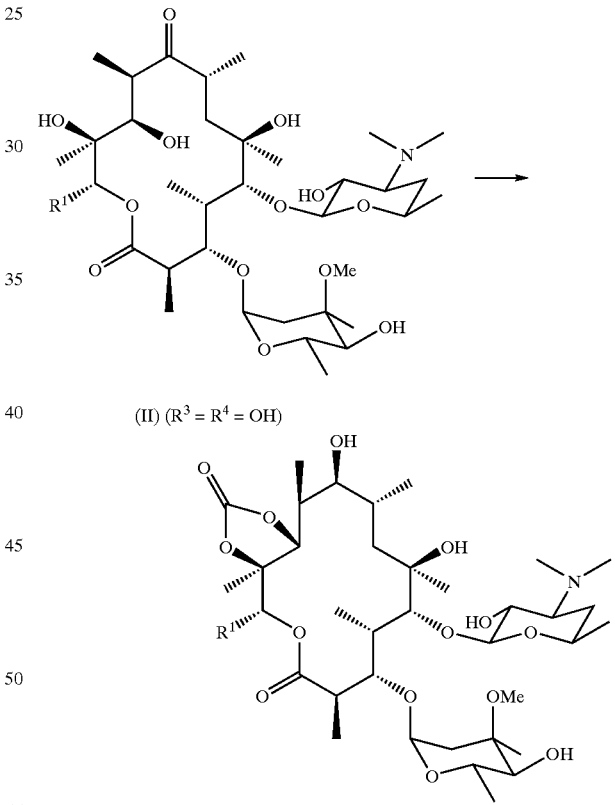

Reaction of the erythromycin (II) wherein $R^3$ and $R^4$ are both OH with a carbonylating reagent, for example ethylene carbonate or 1,1-carbonyldiimidazole, in the presence of a base, for example potassium carbonate or 4-(dimethylamino)pyridine, provides the 11,12-cyclic carbonate. The cyclic carbonates are then converted into the final products according to the method illustrated in Scheme 1.

The erythromycins of formula (II) are prepared as illustrated in Scheme 3 and described in U.S. Pat. Nos. 6,066,721; 6,261,816; and 6,395,710, each of which is incorporated herein by reference.

SCHEME 3

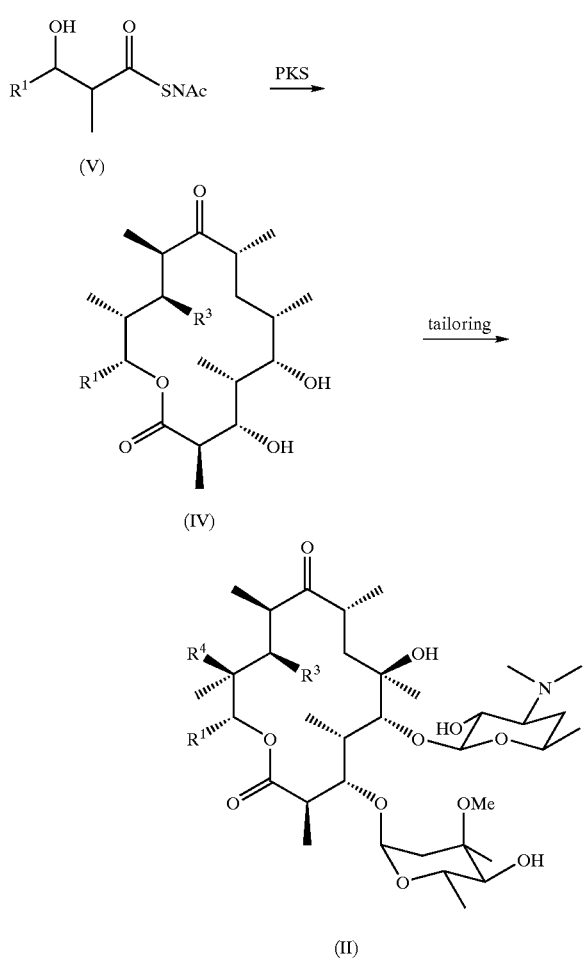

In brief, a diketide thioester of formula (V) is supplied to a polyketide synthase to produce a polyketide of structure (VI). The preparation of diketide thioesters is described in WO 00/44717, which is incorporated herein by reference. In the current invention, the polyketide synthase is a 6-deoxyerythronolide B synthase or an 8,8a-deoxyoleandolide synthase. Suitable examples of 6-deoxyerythronolide B synthases are found in, for example, *Saccharopolyspora erythraea*, as described in U.S. Pat. No. 5,824,513, and in *Micromonospora megalomicea*, as described in WO 01/27284, each of which is incorporated herein by reference. An example of an 8,8a-deoxyoleandolide synthase is found in *Streptomyces antibioticus*, as described in U.S. Pat. No. 6,251,636, incorporated herein by reference. These polyketide synthases are modified so as to prevent the incorporation of their native starter units. Methods of mutating polyketide synthases so as to prevent the incorporation of native starter units, for example by inactivation of the module 1 ketosynthase, are described in U.S. Pat. No. 6,066,721, which is incorporated herein by reference.

While the diketide thioester (V) may be supplied to a cell-free form of the polyketide synthase, as described in U.S. Pat. No. 6,080,555, incorporated herein by reference, it is more convenient to feed (V) to a culture of an organism expressing the mutated polyketide synthase. The organism can be an actinomycete, such as a *Streptomyces* or *Saccharopolyspora*, preferably *Streptomyces coelicolor*, as described in U.S. Pat. No. 6,066,721 and in PCT publication WO 01/83803, or a non-actinomycete such as *Escherichia coli* or *Saccharomyces cerevesiae* as described in WO 01/31035, each of which is incorporated herein by reference. The resulting polyketide (VI) is optionally isolated from the culture medium. A method for this process is detailed in Example 1 below. Using the native polyketide synthases, polyketides with $R^3$=OH are produced.

In one embodiment of the invention, the native polyketide synthase has been mutated so as to produce a polyketide having $R^3$=H. Methods for producing suitable mutated polyketide synthases are described, for example, in U.S. Pat. Nos. 6,391,594 and 6,403,775, both of which are incorporated herein by reference.

Polyketide (VI) is converted into a erythromycin (II) through a series of tailoring steps that include hydroxylation at C-6, addition of mycarose to the 3-OH, addition of desosamine to the 5-OH, hydroxylation at C-12, and methylation at the mycarose 3"-OH. Other forms of the erythromycin can be prepared using the appropriate subset of tailoring enzymes. For example, the erythromycin B ($R^4$=H) is prepared by omitting the hydroxylation at C-12.

This tailoring is most conveniently done by supplying polyketide (VI) to a culture of an organism expressing all the necessary enzymes for the transformations, for example a mutant of *Saccharopolyspora erythraea* comprising an inactive polyketide synthase as described in U.S. Pat. No. 6,395,710, incorporated herein by reference. A method for this process is detailed in Example 2 below.

The compounds of formula (I) are agonists of the motilin receptor. Table 1 shows the $EC_{50}$ values for activation of the motilin receptor, as measured by a calcium-influx assay as described in Carreras et al., *Anal. Biochem.* 300, 146–151 (2002), the disclosure of which is incorporated herein by reference.

TABLE 1

Motilin Receptor Activation

| Compound Ref. | $R^1$ | $R^2$ | $R^3$ | $R^4$ | $EC_{50}$ ($\mu$M) |
|---|---|---|---|---|---|
| Erythromycin A[1] | $CH_3CH_2$ | $CH_3$ | OH | OH | 1.1 |
| A[1] | $CH_3CH_2$ | $CH_3$ | OH | OH | 2.5 |
| B | $CH_3CH_2$ | $CH(CH_3)_2$ | OH | OH | 0.49 |
| C | $FCH_2CH_2$ | $CH_3$ | OH | OH | 5 |
| D | $FCH_2CH_2$ | $CH_2CH_3$ | OH | OH | 2 |
| E | $FCH_2CH_2$ | $CH(CH_3)_2$ | OH | OH | 0.52 |
| F | $CH_3CH_2CH_2$ | $CH_3$ | OH | OH | 8.6 |
| G | $CH_3CH_2CH_2$ | $CH(CH_3)_2$ | OH | OH | 1.4 |
| H | $CH_3CH_2CH_2$ | $C(CH_3)CH_2CH_3$ | OH | OH | 3.3 |
| J | $CH_3CH_2$ | $CH(CH_3)_2$ | H | H | 0.16 |

[1]Comparative compound not according to this invention

Antibacterial activity (Table 2) was determined by in vitro susceptibility tests against *Streptococcus pneumoniae* ATCC 6301, a macrolide-sensitive strain, using methods known in the microbiological art.

TABLE 2

In vitro Minimum Inhibitory Concentrations Against ATCC 6301

| Compound | MIC ($\mu$g/mL) |
|---|---|
| Erythromycin A | 0.03 |
| A | 0.3 |
| F | 1 |

TABLE 2-continued

In vitro Minimum Inhibitory Concentrations Against ATCC 6301

| Compound | MIC (μg/mL) |
|---|---|
| G | >100 |
| J | >100 |

Compounds were tested for motilin receptor desensitization using the cell-based assay described in Carreras et al., US 2002/0192709 A1 (2002), "Methods for Evaluating Therapeutic Efficacy," the disclosure of which is incorporated herein by reference. As shown in Table 3 below, compounds showed little or no desensitization after exposure to 1 or 10 μM amounts of compound tested.

TABLE 3

Motilin Receptor Desensitization

| | Activity following exposure to compound (% of original activity retained) | |
|---|---|---|
| Compound | 1 μM Compound | 10 μM Compound |
| F | 100 | 100 |
| G | 100 | 100 |
| J | 88 | 88 |

Another aspect of the present invention provides methods for the use of compounds having formula (I) in the treatment of impaired gastric motility. In general, methods of using the compounds of the present invention comprise administering to a subject in need thereof a therapeutically effective amount of a compound of the present invention. Illustrative examples of disorders that may be treated with the inventive compounds include but are not limited to gastroparesis, gastroesophageal reflux disease, anorexia, gall bladder stasis, postoperative paralytic ileus, scleroderma, intestinal pseudo-obstruction, gastritis, emesis, and chronic constipation (colonic inertia).

The therapeutically effective amount can be expressed as a total daily dose of the compound or compounds of this invention and may be administered to a subject in a single or in divided doses. The total daily dose can be in amounts, for example, of from about 0.01 to about 10 mg/kg body weight, or more usually, from about 0.1 to about 2 mg/kg body weight. Single dose compositions may contain such amounts or submultiples thereof as to make up the daily dose. In general, treatment regimens according to the present invention comprise administration to a subject in need of such treatment of from about 10 mg to about 1000 mg of the compound(s) of the present invention per day in single or multiple doses.

Typically, the inventive compound will be part of a pharmaceutical composition or preparation that may be in any suitable form such as solid, semisolid, or liquid form. In general, the pharmaceutical preparation will contain one or more of the compounds of the invention as an active ingredient and a pharmaceutically acceptable carrier. Typically the active ingredient is in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. Oral dosage forms may be prepared essentially as described by Hondo et al., 1987, Transplantation Proceedings XIX, Supp. 6: 17–22, incorporated herein by reference.

The carriers that can be used include water, glucose, lactose, gum acacia, gelatin, mannitol, starch paste, magnesium trisilicate, talc, cornstarch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

In summary, the present invention provides motilide compounds, methods for making and methods of using the same, which are further illustrated but not limited by the following examples.

EXAMPLE 1

This example describes the making of 15-methyl-6-deoxyerythronolide B (also referred to as 13-propyl-6-dEB or 15-methyl-6-dEB), an intermediate used in the synthesis of certain compounds of this invention. (Other erythronolides are analogously named; for example the erythronolide with a fluoro group instead of a methyl group at the 15-position is referred to as 15-fluoro-6-dEB.)

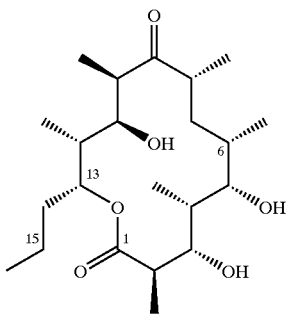

15-Methyl-6-deoxyerythronolide B

A 1 mL vial of the CH999/pJRJ2 (Streptomyces coelicolor that contains a PKS in which the ketosynthase domain of module 1 has been inactivated by mutation) working cell bank is thawed and the contents of the vial are added to 50 mL of Medium 1 in a 250 mL baffled flask.

Medium 1 comprises 45 g/L cornstarch; 10 g/L corn steep liquor; 10 g/L dried, inactivated brewers yeast; and 1 g/L $CaCO_3$. This solution is sterilized by autoclaving for 90 minutes at 121° C. After sterizilization, 1 mL/L of sterile filtered 50 mg/ml thiostrepton in 100% DMSO and 1 mL/L autoclaved 100% antifoam B silicon emulsion (J. T. Baker) are added prior to use.

The flask containing the thawed cells and Medium 1 is placed in an incubator/shaker maintained at 30±1° C. and 175±25 RPM for 48±10 hours. The 50 mL culture is then added to a 2.8 L baffled flask containing 500 mL of Medium 1. This flask is incubated in an incubator/shaker at 30±1° C. and 175±25 RPM for 48±10 hours. The 500 mL culture is than used to inoculate a 10 L fermenter containing 5 L of Medium 1. The fermenter is controlled at 30° C., pH 6.5 by addition of 2.5 N $H_2SO_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 1 at 121° C. for 45 minutes. After the growth period, the contents from the 10 L fermenter are aseptically added to a 150 L fermenter. The fermenter is controlled at 30° C., pH 6.5 by addition of 2.5 N $H_2SO_4$ and 2.5 N NaOH, dissolved oxygen≧80% air saturation by agitation rate (500–700 RPM), air flow rate (10–50 LPM), and/or back pressure control (0.1–0.4 bar). Foam is controlled by the addition of a 50% solution of Antifoam B as needed.

At 35±5 hours, after dissolved oxygen has reached a minimum and $CO_2$ content in fermenter offgas has reached a maximum, (±)-(2R*, 3S*)-2-methyl-3-hydroxyhexanoyl-N-propionylcysteamine (propyl diketide) is added to a final concentration of 4 g/L. Propyl diketide is prepared by dissolving in methylsulfoxide at a ratio of 2:3 (diketide to DMSO) and then filter sterilized (0.2 μm, nylon filter). Production of 15-methyl-6-deoxyerythonolide B (13-propyl-6-dEB) ceases on day 8 and the fermenter is harvested. The fermentation broth is centrifuged at 20,500 g in an Alpha Laval AS-26 centrifuge. The product is predominantly in the supernatant; the centrifuged cell mass is discarded.

After centrifugation, solid phase extraction is performed using HP20 resin (Mitsubishi). Column size is selected based on supernatant volume and titer, so that the loading capacity of 15 g 15-methyl-6-dEB per liter HP20 resin is not exceeded. The centrifuged broth is passed through the resin bed at a linear flow rate of 300±20 cm/h. The pressure on the column should not exceed 15 psi. The resin is then washed with 2 column volumes (CV) of water and then 2 CV of 30% methanol, each at a rate of 300±20 cm/h. 13-propyl-6-dEB is eluted using 7–10 CV 100% methanol at a rate of 300±20 cm/h. During elution, fractions of 1 CV are collected. The fractions are then analyzed, and those containing product are combined to yield a product pool containing >95% of the original 15-methyl-6-dEB in the centrifuged broth. The product pool is reduced to solids using rotary evaporation. Product purity at this stage is 5–35%. Methanol-insoluble material is removed from the product pool by suspending the solids in 3 L 100% methanol per 100 L original broth volume, mixing for 20 minutes, and filtering.

The final purification step is chromatography using HP20SS resin (Mitsubishi). Column size is selected based on amount of product, so that the loading capacity of 15 g 15-methyl-6-dEB per liter HP20SS resin is not exceeded. The filtered methanol solution is diluted by adding an equal volume of water. The 50% methanol solution is passed through the resin bed at a linear flow rate of 300±20 cm/h. The column is then washed with 2 CV of 50% methanol at a rate of 300±20 cm/h. Product is eluted using 12 CV 70% methanol at a rate of 300±20 cm/h. During elution, fractions of 1 CV are collected. The fractions are then analyzed, and those containing >50 mg/L 15-methyl-6-dEB and having >20% chromatographic purity are combined. The product pool is reduced to solids using rotary evaporation. Product purity at this stage is >65% and is suitable for bioconversion to the appropriate erythromycin.

Other modified 6-dEB analogs are prepared according to the same procedure, substituting the appropriate diketde thioester in place of the propyl diketide. Thus, 15-fluoro-6-dEB is prepared using (±)-(2R*, 3S*)-5-fluoro-2-methyl-3-hydroxypentanoyl-N-propionylcysteamine. Also, the syntheses of 15-methyl-6-dEB and 15-fluoro-6-dEB are taught in Ashley et al., WO 00/44717 A2 (2000), the disclosure of which is incorporated herein by reference.

EXAMPLE 2

This example describes the conversion of 15-methyl-6-deoxyerythronolide B to 15-methylerythromycin A (formula II, $R^1$=—$CH_2CH_2CH_3$; $R^3$=$R^4$=OH). Conversion techniques are also taught in Carreras et al., *J. Biotechnology*, 92, 217–228 (2002). the disclosure of which is incorporated by reference.

A 1 mL vial from working cell bank K39-14V (an eryA mutant of *S. erythraea* that is incapable of producing 6-dEB) is thawed and the contents of the vial are added to 50 mL of Medium 2 in a 250 mL baffled flask.

Medium 2 comprises 16 g/L cornstarch; 10 g/L corn dextrin; 15 g/L soy meal flour; 4 g/L $CaCO_3$; 5 g/L corn steep liquor; 6 g/L soy bean oil; 2.5 g/L NaCl; and 1 g/L $(NH_4)_2SO_4$. This solution is sterilized by autoclaving for 60 minutes at 121° C. and 1 mL/L autoclaved 100% antifoam B silicon emulsion (J. T. Baker) is added prior to use.

The flask containing the thawed cells and Medium 2 is placed in an incubator/shaker maintained at 34±1° C. and 175±25 RPM for 48±10 hours. The 50 mL culture is then added to a 2.8 L baffled flask containing 500 mL of Medium 2. The flask is incubated in an incubator/shaker at 34±1° C. and 175±25 RPM for 48±10 hours. The 500 mL culture is than used to inoculate a 10 L fermenter containing 5 L of Medium 2. The fermenter is controlled at 34° C., pH 7.0 by addition of 2.5 N $H_2SO_4$ and 2.5 N NaOH, agitation rate 600 RPM, and air flow rate 1–2 LPM. Foam is controlled by the addition of a 50% solution of Antifoam B as needed. The fermenter culture is allowed to grow under these conditions for 24±5 hours.

A 150 L fermenter is prepared by sterilizing 100 L of Medium 3 at 121° C. for 45 minutes. Medium 3 comprises 17.5 g/L cornstarch; 16 g/L corn dextrin; 16.5 g/L soy meal flour; 4 g/L $CaCO_3$; 6 g/L corn steep liquor; 3 g/L soy bean oil; 3.5 g/L NaCl; and 1 g/L $(NH_4)_2SO_4$. After the growth period, the contents from the 10 L fermenter are aseptically transferred to the 150 L fermenter. The fermenter is controlled at 34° C., pH 7.0 by addition of 2.5 N $H_2SO_4$ and 2.5 N NaOH, dissolved oxygen ≧80% air saturation by agitation rate (500–700 RPM), air flow rate (15–50 LPM), and/or back pressure control (0.1–0.4 bar). Foam is controlled by the addition of a 50% solution of Antifoam B.

At 24±5 hours a 58–60 mL/hour 15% dextrin (w/v) feed is initiated. The dextrin solution is continuously mixed during the feed period. At 24±5 hours 25 grams of 13-propyl-6dEB are added to the fermenter. The 13-propyl-6dEB is prepared by solubolizing 25 grams of 13-propyl-6dEB in 400–600 mL of 100% ethanol and filtering (0.2 μm, nylon filter). Conversion of 13-propyl-6dEB to 13-propyl-erythromycin A ceases after 60±10 hours and the fermenter is harvested. The fermentation broth is centrifuged at 20,500 g in an Alpha Laval AS26 centrifuge. The product is predominantly in the supernatant; the centrifuged cell mass is discarded.

After centrifugation, solid phase extraction is performed using HP20 resin (Mitsubishi). Column size is selected based on supernatant volume and titer, so that the loading capacity of 15 g 15-methylerythromycin A per liter HP20 resin is not exceeded. The centrifuged broth is adjusted to pH 9, then passed through the resin bed at a linear flow rate of 275±5 cm/h. The pressure on the column should not exceed 15 psi. The resin is then washed with 1 column volume (CV) of water at a rate of 275±25 cm/h. The 15-methylerythromycin is eluted using 5 CV 100% methanol at a rate of 275±25 cm/h. During elution, fractions of 1 CV are collected. The fractions are then analyzed, and those containing product are combined to yield a product pool. The product pool is reduced to solids using rotary evaporation.

Methanol-insoluble material is removed from the product pool by suspending the solids in 1L 100% methanol per 100 L original broth volume, adjusting to pH 9, and filtering. The product pool (filtrate) is reduced to solids using rotary evaporation.

The 15-methylerythromycin A is extracted from the product pool (solids) by adding 2 L 4:1 hexane:acetone per 100 L original broth volume, mixing for 20 minutes, and filtering. The remaining solids are extracted the same way two more times and filtrates are combined. The product pool is reduced to solids using rotary evaporation.

The final purification step is chromatography using HP20SS resin (Mitsubishi). Column size is selected based on amount of product, so that the loading capacity of 15 g 15-methylerythromycin A per liter HP20SS resin is not exceeded. The solids from the previous steps are dissolved in 1 L methanol per 100 L original broth volume, and an equal volume of water is added. The 50% methanol solution is passed through the resin bed at a linear flow rate of 275±25 cm/h. The column is then washed with 1 CV of 50% methanol, then 3 CV 60% methanol, each at a rate of 275±25 cm/h. Product is eluted using 3 CV 70% methanol, then 10 CV 75% methanol, each at a rate of 275±25 cm/h. During elution, fractions of 1 CV are collected. The fractions are then analyzed, and those containing 15-methylerythromycin A are combined. The product pool is reduced to solids using rotary evaporation.

Other modified erythromycins are prepared using the same procedure and substituting the appropriate 6-dEB analog in place of 15-methyl-6-dEB. Thus, 15-fluoroerythromycin A is prepared using 15-fluoro-6-dEB.

EXAMPLE 3

This example describes a general method for the preparation of (9S)-9-dihydroerythromycins (formula II), with reference to Scheme 1.

A solution of the erythromycin (0.36 mmol) in 1:3 ethanol/ether (20 mL) is cooled to −15° C. and treated with sodium borohydride (0.9 mmol). The reaction is allowed to warm slowly to ambient temperature over 4 hours. The excess borohydride is destroyed by addition of phosphate buffer, pH 6, and 10 mL of triethanolamine is added. After 1 hour, the mixture is extracted with ethyl acetate, dried over $MgSO_4$, filtered, and concentrated to dryness under reduced pressure. The product is purified by silica gel chromatography using 1:1 acetone-hexanes with 1% triethylamine. The following compounds were prepared using this procedure:

(9S)-9-dihydroerythromycin A;
(9S)-9-dihydro-15-methylerythromycin A; and
(9S)-9-dihydro-15-fluoroerythromycin A.

EXAMPLE 4

This example describes a general procedure for the preparation of N-desmethyl-(9S)-9-dihydroerythromycins (formula III), with reference to Scheme 1.

Sodium acetate trihydrate (139 mg) and iodine (52 mg) are added sequentially to a solution of the (9S)-9-dihydroerythromycin (150 mg) in 10 mL of 8:2 methanol/water. A 0.2 M solution of LiOH (1 mL) is added in 4 portions over 1 hour. Complete reaction is determined by thin-layer chromatographic analysis. Excess reagents are quenched by addition of saturated sodium thiosulfate solution, and the volatiles are removed under reduced pressure and the mixture is extracted with ethyl acetate. The organic phase is washed with saturated $NaHCO_3$, dried over $Na_2SO_4$, filtered, and concentrated to give the crude product. Silica gel chromatography (acetone/hexanes+2% $Et_3N$) gives the pure product. The following compounds were prepared using this procedure:

N-desmethyl(9S)-9-dihydroerythromycin A;
N-desmethyl(9S)-9-dihydro-15-methylerythromycin A; and
N-desmethyl(9S)-9-dihydro-15-fluoroerythromycin A.

EXAMPLE 5

This example describes the preparation of N-desmethyl-N-$R^2$-(9S)-9-dihydroerythromycins, with particular reference to Scheme 1, compounds having formula II ($R^3$=$R^4$=OH).

A mixture of the N-desmethyl(9S)-9-dihydro-erythromycin A analog (0.035 mmol), diisopropylethylamine (62.5 uL), $R^2I$ (1.3 mmol), and acetonitrile (1 mL) is sealed and stirred at 70° C. overnight. The mixture is cooled, diluted with aqueous $NaHCO_3$, and extracted with ethyl acetate. The extract is dried over $MgSO_4$, filtered, and evaporated to dryness. The product is purified by silica gel chromatography using 2:1 hexanes/acetone+1% $Et_3N$. The following compounds were prepared according to this procedure:

(a) N-desmethyl-N-ethyl(9S)-9-dihydro-15-fluoroerythromycin A, using N-desmethyl(9S)-9-dihydro-15-fluoroerythromycin A and ethyl iodide;

(b) N-desmethyl-N-isopropyl(9S)-9-dihydro-15-fluoroerythromycin A, using N-demethyl(9S)-9-dihydro-15-fluoroerythromycin A and isopropyl iodide;

(c) N-desmethyl-N-isopropyl(9S)-9-dihydro-15-methylerythromycin A, using N-demethyl(9S)-9-dihydro-15-methylerythromycin A and isopropyl iodide; and (d) N-desmethyl-N-(2-butyl) (9S)-9-dihydro-15-methylerythromycin A, using N-demethyl(9S)-9-dihydro-15-methylerythromycin A and 2-iodobutane.

EXAMPLE 6

This example illustrates the demethylation step of the Scheme 1A, with specific reference to N-desmethyl-15-methylerythromycin A (compound III'; $R^1$=1-propyl; $R^3$=$R^4$=OH), although it is to be understood that the procedure is generally applicable to other analogous compounds.

A mixture of 15-methylerythromycin A (compound $II^1$, $R^1$=1-propyl; $R^3$=$R^4$=OH; 5.00 g, 6.15 mmol) and sodium acetate trihydrate (4.18 g, 30.75 mmol) in methanol-water (8:2 V/V, 100 mL) was stirred at 50° C. Iodine (1.56 g, 6.15 mmol) was then added. During the reaction 1N sodium hydroxide (6.15 mL) was added in small portions. Complete reaction was determined by thin-layer chromatographic analysis. After removal of solvent, the mixture was extracted three times with ethyl acetate, dried over sodium sulfate. Crude product (4.97 g) was obtained as a yellow solid, which was used for next step without further purification.

EXAMPLE 7

This example illustrates the alkylation step of Scheme 1A, with specific reference to N-desmethyl-N-isopropyl-15-methylerythromycin A (compound IV', $R^1$=1-propyl;

$R^2$=isopropyl; $R^3$=$R^4$=OH), though it is to be understood that the procedure is generally applicable to other analogous compounds.

A mixture of the crude N-desmethyl-15-methylerythromycin A from the previous example (2.50 g, 3.41 mmol), diisopropylethylamine (6.1 mL, 10 equiv), 2-iodopropane (10.2 mL, 30 equiv) in acetonitrile (50 mL) was heated in a 70° C. bath for 24 h. Water and saturated sodium bicarbonate were added. The solution was extracted three times with ethyl acetate and dried over magnesium sulfate. The crude product was purified via silica gel column chromatography (3:1 hexane-acetone, 1% triethylamine) to give pure N-desmethyl-N-isopropyl-15-methylerythromycin A (1.80 g, 75% yield for 2 steps).). m/z: 777.0 (MH); $^{13}$C-NMR (CDCl$_3$): 221.86, 175.62, 103.11, 96.15, 83.30, 79.85, 78.01, 75.10, 74.90, 74.59, 72.58, 70.35, 68.91, 68.75, 65.48, 62.79, 52.49, 49.47, 45.12, 44.76, 39.32, 38.43, 37.85, 34.96, 33.06, 30.76, 30.19, 26.93, 21.48, 21.41, 20.99, 20.46, 19.47, 18.62, 18.27, 16.15, 15.84, 14.00, 12.04, 9.01.

EXAMPLE 8

This example illustrates the carbonyl reduction step of Scheme 1A, with particular reference to N-desmethyl-N-isopropyl-15-methyl-(9S)-9-dihydroerythromycin A (compound I, $R^1$=1-propyl; $R^2$=isopropyl; $R^3$=$R^4$=OH), although it is to be understood that the procedure is generally applicable to other analogous compounds.

N-desmethyl-N-isopropyl-15-methylerythromycin A (1.74 g, 2.24 mmol) was dissolved in methanol-ether (1:3 V/V, 50 mL), then cooled to −20° C. Sodium borohydride (189 mg, 5.0 mmol) was added. The mixture was then warmed slowly to room temperature over a period of 3 h. The excess sodium borohydride was destroyed by addition of pH 6.0 phosphate buffer, followed by triethanolamine (10 mL). After 30 min the mixture was extracted with ethyl acetate and dried over magnesium sulfate. The crude product was purified by silica gel column chromatography (3:1 hexane-acetone with 1% triethylamine). Pure N-desmethyl-N-isopropyl-15-methyl-(9S)-9-dihydroerythromycin A (1.63 g, 93% yield) was obtained. m/z: 779.0 (MH); $^{13}$C-NMR (CDCl$_3$): 177.28, 102.59, 95.81, 83.45, 82.76, 78.81, 77.86, 75.68, 75.03, 74.67, 72.68, 70.38, 70.24, 69.26, 65.97, 62.28, 52.52, 49.34, 44.83, 42.00, 36.78, 34.80, 34.37, 33.01, 31.96, 31.02, 30.76, 25.46, 21.58, 21.28, 21.10, 20.41, 19.93, 19.74, 18.27, 16.37, 14.86, 14.30, 14.02, 9.17.

EXAMPLE 9

This example describes the construction of a strain of Saccharopolyspora erythraea (K24-1/159-44) capable of the biosynthesis of 11-deoxyerythromycins, with particular reference to 11-deoxyerythromycin B, which are useful as intermediates for the synthesis of certain compounds of this invention.

11-Deoxyerythromycin B can be prepared in a single fermentation in a genetically engineered host cell expressing a modified version of the DEBS suite of genes (eryAI, eryAII, and eryAIII). The eryAI gene is engineered by replacement of the ketoreductase domain in module 2 with a cassette containing a dehydratase domain, an enoylreductase domain, and a ketoreductase domain, for example taken from module 1 of the rapamycin PKS. Methods for domain replacement are provided in, for example, McDaniel, U.S. Pat. No. 6,403,775 (2002), which is incorporated herein by reference. The engineered eryAI gene is incorporated along with the eryAII and eryAIII genes into a host cell competent in the production of erythromycins once the engineered PKS genes have been added. In preferred embodiments, these host cells are "clean hosts," wherein their native PKS genes have been removed. Examples of suitable hosts include but are not limited to the clean host Saccharopolyspora erythraea K24-1 and strains of Saccharopolyspora erythraea having mutated PKS genes such as those described in Santi et al., US 2002/0004229 A1 (2002), which is incorporated herein by reference. Strain K24-1 has had the native eryAI, eryAII, and eryAIII genes replaced with the attB phage attachment site of the actinophage ΦC31, described in U.S. Pat. No. 5,190,871, incorporated herein by reference, and followed by the ermE* promoter. This allows plasmid vectors comprising the complementary attP phage attachment site along with the genes to be delivered to integrate into the chromosome at the attB site in the presence of a phage integrase. Examples of suitable integrating phage vectors include but are not limited to pSET152 and its derivatives.

Preparation of starting host strain Saccharopolyspora erythraea K24-1 is described in Santi et al., US 2002/0004229 A1 (2002), and the strain was deposited with the American Type Culture Collection, P.O. Box 1549, Manassas, Va. 20108, USA, according to the terms of the Budapest Treaty on Mar. 12, 2003, with accession number PTA-5061.

pKOS159-8 and pKOS159-10 are derivatives of pSET152 containing the eryA genes under the control of the ermEp* promoter and the actIp/actII-ORF4 promoter-activator pair, respectively. A 35 kb NsiI fragment from pKAO127 carrying the eryA genes and the actIp/actII-ORF4 region was cloned into pKOS97-64c (a pSET152 derivative containing the ermEp* promoter and a λ cos site) to make pKOS159-10. The fd transcriptional terminator from the pKAO127 fragment prevents expression of any genes from the ermEp* promoter in this plasmid. The fragment containing the fd terminator and actIp/actII-ORF4 segment in pKOS159-10 was removed by digestion with PacI and self-ligation to generate pKOS159-8. For expression of eryA genes under their natural promoter, pKOS159-31 was constructed by cloning the NdeI-XbaI fragment carrying the eryA genes (and λ cos site) from pKOS159-10 and the XbaI-NdeI digested PCR amplified eryAI left flank fragment from above into pSET152 digested with XbaI. pKOS159-33, which contains the eryA genes from S. erythraea K41-135 was constructed in an analogous way using the eryA fragment from pKOS108-04. Likewise, all engineered DEBS expression plasmids were made using pKOS159-31 as a scaffold and appropriate restriction enzymes to move the genetically modified eryA fragment from existing plasmids.

pKOS15944 is a pSET152 (Bierman et al., Gene 116, 43–49 (1992), "Plasmid cloning vectors for the conjugal transfer of DNA from Escherichia coli to Streptomyces spp.") derivative plasmid that has genetically modified eryA genes (KR2→rapDH/ER/KR1) under the control of eryAI promoter (Rodriguez et al., J. Ind. Microbio. Biotechnol., "Rapid Engineering of Polyketide Overproduction by Gene Transfer to Industrially Optimized Strains," web-published as document no. 10.1007/s10295-003-0045-1 (http://link.springer-ny.com) (16 Apr. 2003)). A 30 kb NdeI-NsiI fragment (carrying genetically modified enjA genes) from pKOS11-66 (Xue et al., *Proc. Natl. Acad. Sci. U.S.A.,* 96, 11740–11745 (1999), "A multiplasmid approach to preparing large libraries of polyketides") was isolated and ligated to a 8 kb NdeI-NsiI fragment from pKOS159-33 (Rodriguez et al., cited supra), containing the vector pSET152, eryAp promoter and cos λ site). The ligation mixture was packaged using Gigapack III Gold packaging extract (Stratagene), and used to infect *E. coli* XL-1 Blue. Recombinats were selected on LB agar plates containing 60 μg/ml apramycin. pKOS15944 plasmid DNA was isolated and checked by restriction digestions.

*S. erythraea* strain K24-1, which contains a chromosomal deletion of the three eryA genes and insertion of the attB loci for the Streptomyces phage φC31 from *Streptomyces lividans*, followed by the ermE* promoter in their place, was prepared by harvesting spores from strains grown on 1–2 M1 plates (per liter, 5 g glucose, 5 g tryptone, 0.5 g betaine hydrochoride, 5 g corn starch, 1 g corn steep liquor (50%), 200 mg $MgSO_4 \cdot 7H_2O$, 2 mg $ZnSO_4 \cdot 7H_2O$, 0.8 mg $CuSO_4 \cdot 5H_2O$, 0.2 mg $CoCl_2 \cdot 6H_2O$, 4 mg $FeSO_4 \cdot 7H_2O$, 80 mg $CaCl_2 \cdot 6H_2O$, 150 mg $KH_2PO_4$, 10 g NaCl, 20 g agar) filtering the spores through sterile cotton, and resuspending in 1 ml of 20% glycerol. Spore suspensions were stored at −20° C. A 20 μL aliquot of the spore suspension was added to 5 mL of 2×YT and incubated at 30° C. with shaking. After 1 h the spores were collected by centrifugation (recipient cells). Donor cells were prepared by transforming *E. coli* ET12567/pUZ8002 with pKOS159-44 and selecting for apramycin resistance only. Several colonies were picked off the primary transformation plate and used to inoculate 5 ml of LB with chloramphenicol (10 μg/mL) kanamycin (100 μg/mL) and apramycin (60 μg/mL). The cells were grown at 37° C. for 3–4 h ($OD_{600}$ of 0.4–0.6), collected by centrifugation, washed in 5 mL LB, centrifuged, and resuspended in 100 μL of LB. Conjugal transfer between the donor and recipient cells was performed by resuspending the recipient cells in the 100 μl donor suspension and the cells were spread on R5 plates (Hopwood et al., *Genetic Manipulation of Streptomyces: A Laboratory Manual* (The John Innes Foundation, Norwich, UK, 1985) containing 50 μg/mL nalidixic acid and incubated at 34° C. for 16 h. The plates were then overlayed with 3 mL of soft nutrient agar containing 1 mg nalidixic acid and 2 mg apramycin. Exconjugants K24-1/159-44 were observed after 48 h of further incubation.

Strain K24-1/159-44 was deposited with the American Type Culture Collection, P.O. Box 1549, Manassas, Va. 20108, USA, according to the terms of the Budapest Treaty on Mar. 12, 2003, with accession number PTA-5054.

EXAMPLE 10

This example describes the biosynthesis of 11-deoxyerythromycin B, an intermediate for the synthesis of certain compounds of this invention, using the strain described in the preceding example.

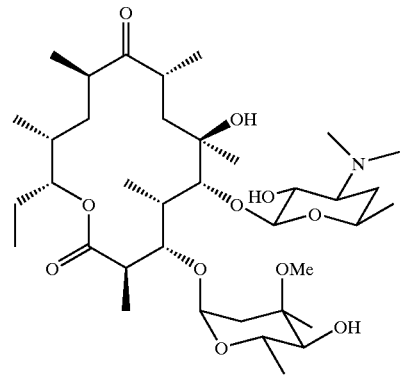

11-Deoxyerythromycin B

Fermentation techniques disclosed in Frykman et al., *Biotechnol. Bioeng.,* 76, 303–310 (2001) "Precursor-Directed Production of Erythromycin Analogs by *Saccharopolyspora erythraea*," and Rodriguez et al., cited supra, the disclosures of which are incorporated by reference, were followed.

The following media were used: (a) Seed medium V1 contained 16 g/L corn starch, 10 g/L dextrin (D-2256, Sigma-Aldrich), 15 g/L soybean flour (S-9633, Sigma-Aldrich), 2.5 g/L sodium chloride, 5 g/L corn steep liquor, 1 g/L ammonium sulfate (A-2939, Sigma-Aldrich), 6 g/L soybean oil (S-7381, Sigma-Aldrich), and 4 g/L calcium carbonate (C-4830, Sigma Aldrich). (b) Fermentation medium F2 contained 28 g/L corn starch, 24 g/L soybean meal, 5.5 g/L sodium chloride, 8 g/L corn steep liquor, and 1.5 g/L ammonium sulfate, 4.5 g/L soybean oil, and 6 g/L calcium carbonate. All media were sterilized by autoclaving at 121° C. for 90 min.

Two seed flasks were started by taking a 1 mL vial of *Saccharopolyspora erythraea* K24-1/pKOS159-44 from a frozen cell bank, thawing, and adding the vial contents into 50 mL of medium V1 and incubating at 34° C. for 40–48 h. Two secondary seeds were then created by transferring 50 mL aliquots from the seed flask to 500 mL of medium V1 and incubating at 34° C. for 40–48 h.

Both 500 mL secondary seed cultures were transferred to a B. Braun B10 fermenter containing 9 L of medium V1. The fermenter was operated at 34° C. and maintained at pH 7.0 by addition of 2.5 N sulfuric acid and 2.5 N sodium hydroxide. Aeration at 3 LPM and agitation at 600 to 800 rpm were provided, maintaining the dissolved oxygen tension at greater than 40%. Harvesting took place after about 24 h.

Then, 10 L of the fermenter seed culture was transferred to a B. Braun Biostat UD500 fermenter containing 300 L medium F2. The Biostat UD500 fermenter was operated at 34° C. and maintained at pH 7.0 by the addition of 2.5 N sulfuric acid and 2.5 N sodium hydroxide. Agitation at 200–300 rpm and aeration at 40–250 LPM were provided, maintaining the dissolved oxygen tension at greater than 40%. Dextrin (150 g/L) was fed at a rate of 675 mL/h from 24 to 98 h. Soybean oil was fed at a rate of 64 mL/h from 24 to 140 h. n-Propanol was fed at a rate of 26 mL/h from 24 to 140 h. Harvesting took place after 180 h.

Foaming was controlled by the addition of a 50% solution of antifoam B (J T Baker) as needed.

The fermentation broth was clarified by centrifugation and was subjected to solid phase extraction using HP20 resin (Mitsubishi). Adsorbed product was eluted with methanol and dried. The crude product was then subjected to ethyl acetate:water liquid:liquid extraction. The combined ethyl acetate extracts were dried. The product was purified by chromatography using HP20SS resin, eluting with a step-gradient from 50% to 80% methanol. The product containing fractions were pooled and dried, to provide 11-deoxyerythromycin B. m/z: 702.64 (MH); $^{13}$C-NMR (CDCl$_3$): 219.13, 175.56, 102.48, 95.92, 82.73, 79.40, 78.92, 77.79, 74.88, 72.52, 70.79, 68.80, 65.52, 65.13, 49.25, 45.98, 44.31, 43.40, 40.15 (2×), 38.11, 37.20, 36.54, 34.79, 33.19, 28.52, 26.37, 24.55, 21.37, 21.19, 18.54, 18.31, 15.69, 14.68, 11.96, 10.36, 9.16 ppm.

EXAMPLE 11

This example describes the conversion of 11-deoxyerythromycin B to N-desmethyl-N-isopropyl-11-deoxy-(9S)-9-dihydroerythromycin B (compound I, R$^1$=ethyl, R$^2$=isopropyl, and R$^3$=R$^4$=H; compound J, Table 1), using the approach of Scheme 1.

11-Deoxyerythromycin B (200 mg, 0.285 mmol) was reduced generally following the procedure of Example 8 to give (9S)-9-dihydroerythromycin B (94 mg, 47% yield). m/z: 705.0 (MH); $^{13}$C-NMR (CDCl$_3$): 176.82, 102.38, 95.82, 83.04, 80.95, 80.23, 79.01, 77.82, 74.89, 72.71, 70.89, 69.14, 66.04, 65.12, 49.28, 44.67, 42.23, 40.28 (2×), 37.36, 34.81 (2×), 33.50, 32.58, 29.39, 28.90, 25.29, 25.17, 21.53, 21.16, 20.04, 18.13, 17.98, 13.82, 10.59, 10.22, 9.24.

Generally following the procedures of Examples 6 and 7, 11-deoxy(9S)-9-dihydroerythromycin B (94 mg, 0.134 mmol) was then converted to N-desmethyl-N-isopropyl-11-deoxy-(9S)-9-dihydroerythromycin B (57 mg, 58% yield). m/z: 733.0 (MH); $^{13}$C-NMR (CDCl$_3$): 176.98, 102.05, 95.55, 82.33, 81.11, 80.22, 78.90, 77.89, 74.93, 72.69, 70.29, 69.11, 65.98, 65.16, 52.53, 49.28, 44.52, 42.38, 37.27, 34.91, 34.73, 33.38, 32.96, 32.60, 30.99, 29.38, 25.18 (2×), 21.54, 21.22, 21.05, 20.34, 19.91, 18.12, 17.85, 13.68, 10.45, 10.21, 9.10.

The invention having now been described by way of written description and examples, those of skill in the art will recognize that the invention can be practiced in a variety of embodiments and that the foregoing description and examples are for purposes of illustration and not limitation of the following claims. Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference.

Citation of publications or documents above is not intended as an admission that any of the cited publications or documents is pertinent prior art, nor does it constitute any admission as to the contents or date of these publications or documents.

What is claimed is:

1. A compound having the formula (I)

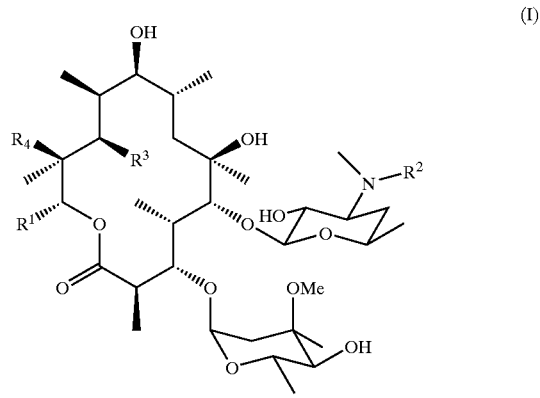

and the pharmaceutically acceptable salts, esters, and prodrug forms thereof, wherein R$^1$ is substituted or unsubstituted C$_1$–C$_{10}$ alkyl, substituted or unsubstituted C$_2$–C$_{10}$ alkenyl, substituted or unsubstituted C$_2$–C$_{10}$ alkynyl, substituted or unsubstituted aryl, or substituted or unsubstituted heterocyclo;

R$^2$ is H, substituted or unsubstituted C$_1$–C$_5$ alkyl, substituted or unsubstituted C$_2$–C$_5$ alkenyl, substituted or unsubstituted C$_2$–C$_5$ alkynyl, substituted or unsubstituted aryl, or substituted or unsubstituted heterocyclo;

R$^3$ is H or OH; and

R$^4$ is H or OH, or R$^3$ and R$^4$ taken together form O—(C=O)—O;

with the proviso that when (a) R$^1$ is ethyl and (b) R$^3$ is OH or R$^3$ and R$^4$ taken together form O—C(=O)—O, then R$^2$ is not H or methyl.

2. A compound according to claim 1 wherein

R$^1$ is substituted or unsubstituted C$_1$–C$_{10}$ alkyl, substituted or unsubstituted C$_2$–C$_{10}$ alkenyl, substituted or unsubstituted C$_2$–C$_{10}$ alkynyl, substituted or unsubstituted aryl, or substituted or unsubstituted heterocyclo;

R$^2$ is H, ethyl, propyl, isopropyl, or 2-butyl; and

R$^3$ and R$^4$ are OH, with the proviso that when R$^1$ is ethyl, then R$^2$ is not H or methyl.

3. A compound according to claim 1 wherein:

R$^1$ is substituted or unsubstituted C$_1$–C$_5$ alkyl;

R$^2$ is H, substituted or unsubstituted C$_1$–C$_5$ alkyl, substituted or unsubstituted C$_2$–C$_5$ alkenyl, or substituted or unsubstituted C$_2$–C$_5$ alkynyl; and R$^3$ and R$^4$ are OH, with the proviso that when R$^1$ is ethyl, then R$^2$ is not H or methyl.

4. A compound according to claim 1 wherein:

R$^1$ is ethyl;

R$^2$ is ethyl, propyl, isopropyl, or 2-butyl; and

R$^3$ and R$^4$ are OH.

5. A compound according to claim 1 wherein:

$R^1$ is substituted ethyl;

$R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; and $R^3$ and $R^4$ are OH.

6. A compound according to claim 1 wherein:

$R^1$ is substituted ethyl;

$R^2$ is H, ethyl, propyl, isopropyl, or 2-butyl; and $R^3$ and $R^4$ are OH.

7. A compound according to claim 1 wherein:

$R^1$ is propyl;

$R^2$ is H, substituted or unsubstituted $C_1$–$C_5$ alkyl, substituted or unsubstituted $C_2$–$C_5$ alkenyl, or substituted or unsubstituted $C_2$–$C_5$ alkynyl; and $R^3$ and $R^4$ are OH.

8. A compound according to claim 1, wherein $R^3$ and $R^4$ are independently H or OH;

$R^1$ is selected from the group consisting of ethyl, 2-fluoroethyl, and 1-propyl; and $R^2$ is selected from the group consisting of methyl, ethyl, isopropyl, and 2-butyl;

with the proviso that when $R^1$ is ethyl and $R^3$ is OH, then $R^2$ is not methyl.

9. A compound according to claim 1, wherein $R^1$, $R^2$, $R^3$ and $R^4$ are according to the combinations set forth in the table below:

| $R^1$ | $R^2$ | $R^3$ | $R^4$ |
|---|---|---|---|
| $CH_3CH_2$ | $CH(CH_3)_2$ | OH | OH |
| $FCH_2CH_2$ | $CH_3$ | OH | OH |
| $FCH_2CH_2$ | $CH_2CH_3$ | OH | OH |
| $FCH_2CH_2$ | $CH(CH_3)_2$ | OH | OH |
| $CH_3CH_2CH_2$ | $CH_3$ | OH | OH |
| $CH_3CH_2CH_2$ | $CH(CH_3)_2$ | OH | OH |
| $CH_3CH_2CH_2$ | $C(CH_3)CH_2CH_3$ | OH | OH |
| $CH_3CH_2$ | $CH(CH_3)_2$ | H | H |

10. A compound according to claim 1 selected from the group consisting of:

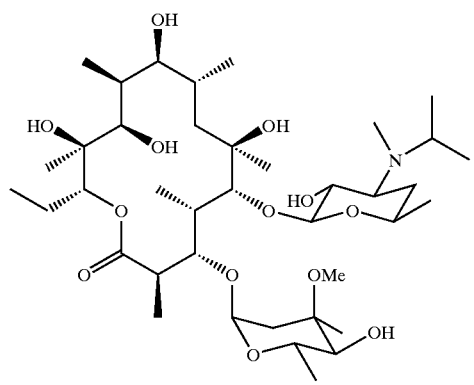

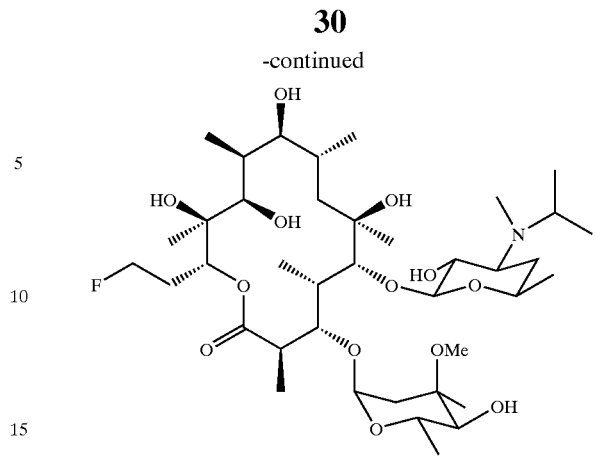

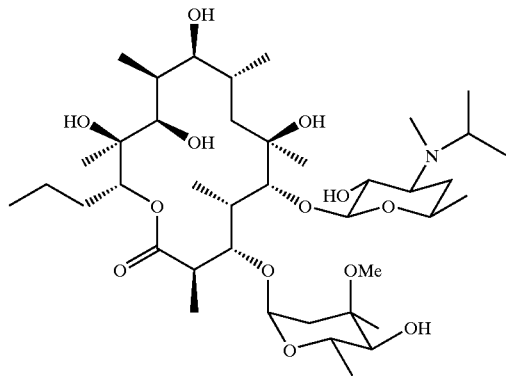

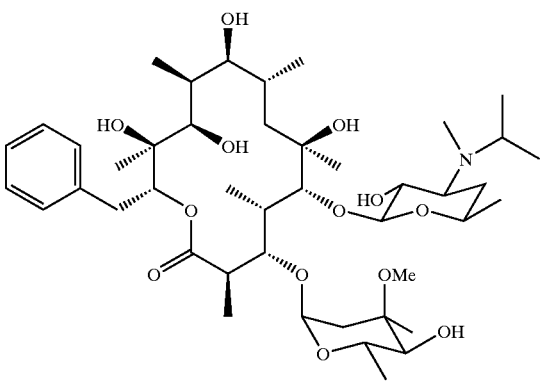

-continued

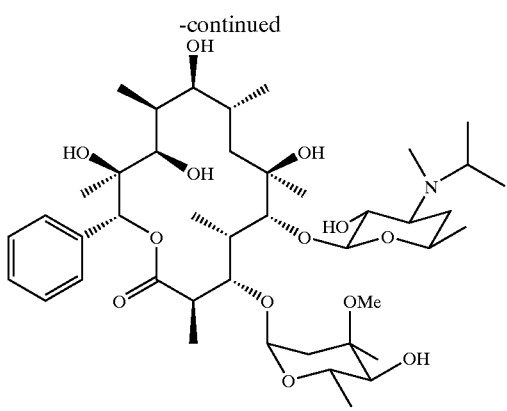

and

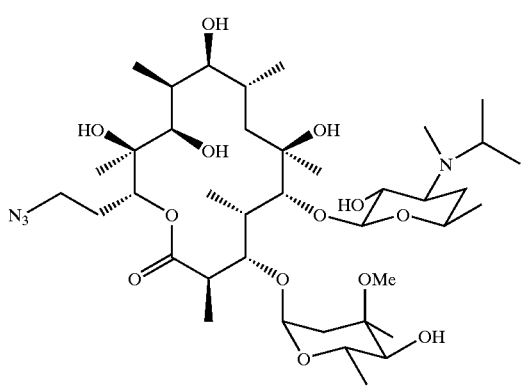

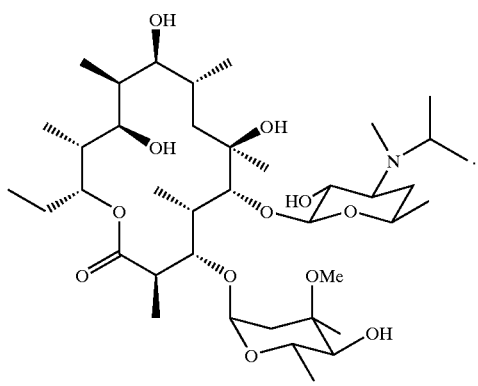

11. A compound according to claim 1, having a structure of the formula:

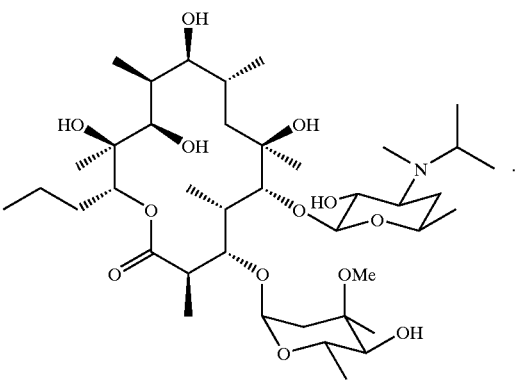

12. A compound according to claim 1, having a structure of the formula:

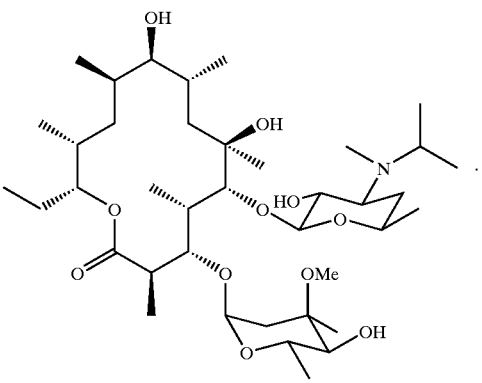

13. A pharmaceutical composition consisting of a therapeutically effective amount a compound according to claim 1 together with a pharmaceutically acceptable carrier.

14. A method for the treatment of a disorder of gastric motility, when the disorder is gastroparesis or gastroesophegeal reflux disease, in a patient suffering therefrom, comprising administering to the patient a therapeutically effective dose of a composition of claim 1.

* * * * *